US00PP09452P

United States Patent [19]

Drewlow

[11] Patent Number: Plant 9,452

[45] Date of Patent: Feb. 13, 1996

[54] POINSETTIA PLANT NAMED 'RED DELIGHT'

[75] Inventor: Lyndon W. Drewlow, Ashtabula, Ohio

[73] Assignee: Mikkelsens Inc., Ashtabula, Ohio

[21] Appl. No.: 383,841

[22] Filed: Feb. 6, 1995

[51] Int. Cl.[6] ..... A01H 5/00

[52] U.S. Cl. ..... Plt./86.4

[58] Field of Search ..... Plt./86.4

*Primary Examiner*—James R. Feyrer

*Attorney, Agent, or Firm*—Foley & Lardner

[57] ABSTRACT

A distinct cultivar of poinsettia plant named Red Delight, characterized by the combined traits of red bract color, thick and well-branched plant habit, vigorous growth, medium green foliage, and early flowering response.

1 Drawing Sheet

The present invention relates to a new and distinctive cultivar of poinsettia plant, botanically known as *Euphorbia pulcherrima,* and known by the cultivar name Red Delight.

The new cultivar was developed by the inventor Lyndon Drewlow through a controlled breeding program carried out in Ashtabula, Ohio by crossing Mikkelsen Seedling No. 89-322-3 (seed parent) with Mikkelsen Seedling No. 88-207-4 (pollen parent), both proprietary cultivars used in this breeding program.

The non-branching red bract seedling (90-470-2) of the stated cross was then grafted to the excellent branching type cultivar Rochford Improved in an attempt to transfer the branching habit of Rochford Improved to the red seedling. The graft was successful, resulting in the seedling having the branching habit of Rochford Improved and retaining all other desirable characteristics.

Asexual reproduction by stem cuttings has shown that the unique features of this new poinsettia are stabilized and are reproduced true to type in successive propagations.

The following characteristics distinguish the new poinsettia from both its parent cultivars and other cultivated poinsettia of this type known and used in the floriculture industry, including seedling 90-470-2 resulting from the described cross, and the cultivar Rochford Improved, Donner (U.S. Plant Pat. No. 8,563), and Feliz Navidad (U.S. Plant Pat. No. 8,260), to which comparative reference is made.

1. When 5 or more nodes are left after a pinch (apical tip removal), Red Delight will develop full-length shoots from each node, similar to Rochford Improved, Donner, and Feliz Navidad, while the original seedling 90-470-2 will develop a full-length shoot from only the upper three (3) nodes, with the balance of shoots being greatly repressed.

2. Red Delight at 24 to 26 cm is shorter than the 90-470-2 seedling (28 to 30 cm) when similar size plants are left after pinching. This is because there is little or no apical dominance in Red Delight or the other branched types, resulting in the lower breaks growing longer than top breaks on a plant instead of the top three (3) shoots becoming dominant. Rochford Improved is taller at 34 to 36 cm. Feliz Navidad and Donner are similar in height at 24 to 26 cm.

3. Red Delight has slightly lighter green leaves than the original seedling 90-470-2 but is similar in leaf color to Rochford Improved, Donner, and Feliz Navidad. Despite the slight difference in color, all would be classified 147A (R.H.S. Colour Chart).

4. Red Delight is very tolerant to low light levels and high temperatures of the average home or commercial buliding. When kept moist, its leaves do not yellow and drop like seedling 90-470-2. This trait is similar to Rochford Improved, and better than Donner and Feliz Navidad.

5. Bract coloration of Red Delight is 45A to 45B (R.H.S.), which is a lighter red than seedling 90-470-2 (45A). Feliz Navidad is a lighter red (45B to 45C) than Red Delight, while Donner is a deeper red (46B to 46C).

6. Red Delight has a cyathia cluster that is slightly smaller in number and diameter (2.0 to 2.5 cm) than original seedling 90-470-2; much smaller than Rochford Improved, and similar to Donner and Feliz Navidad.

7. Red Delight is resistant to heat delay of flower bud initiation under night temperatures above 23° C., similar to seeding 90-470-2, Feliz Navidad and Donner, with Rochford Improved being very susceptible. This is of commercial importance, especially in the South and during warmer than normal falls in the North.

8. Bract size of Red Delight is similar to Donner and Feliz Navidad at 30 to 32 cm, which is larger than Rochford Improved at 20 to 25 cm. The bracts are not reflexed like Donner and Feliz Navidad but flat like Rochford Improved. Cyathia will not split apart like Rochford Improved but remain in a tight cluster like Donner and Feliz Navidad.

9. Essentially all other characteristics of Red Delight are similar to the characteristics of original seedling 90-470-2, including early flowering under natural short days, similar shaped leaves and bracts, retention of cyathia under stress conditions, and non-splitting cyathia.

The accompanying color photographic drawing comprises a top perspective view of a plant of Red Delight, which colors being as true as it is reasonably possible to obtain in a color reproduction of this type. The photograph was taken on Dec. 21, 1994 in a double polyethylene plastic covered greenhouse in Ashtabula, Ohio on a clear day.

The following is a detailed description of Red Delight based on plants produced in greenhouses in Ashtabula, Ohio during the fall season of the year. Plants were grown in 15 cm pots and measurements were taken 16 weeks after rooted cuttings were planted. Height measurements were taken from the soil line of the container. The plants were grown at 64°–68° F. night temperatures under 3500–4000 foot candles of light and at nutritional levels of 250 ppm Nitrogen, 75 ppm Potassium, and 250 ppm Phosphorous, with trace elements added. Habit of growth, foliage coloration, leaf variegation, size of leaves and flower size are influenced by nutritional and environmental conditions. Color references are made to The Royal Horticultural Society Colour Chart except where general terms of ordinary dictionary significance are used.

Parentage: Controlled cross of female Mikkelsen Seedling No. 89-322-3 and Mikkelsen Seedling No. 88-207-4. The non-branching seedling (90-470-2) from the cross was then grafted to a plant of Rochford Improved in an effort to produce a plant having the same excellent branching characteristics as Rochford Improved.

Classification: *Euphorbia pulcherrima,* cv, Red Delight.

Propagation:

*Type cutting.*—Stem 5 to 6 cm long.

*Time to root.*—14 Days at 21° C. summer; 18 days at 21° C. winter.

*Rooting habit.*—Abundant thick fibrous roots.

Plant description:

*Form.*—Extremely upright; when apical meristem is removed by pinching leaving five (5) or more nodes above soil line of pot, generally all lateral shoots will emerge and develop, with lower shoot breaking first.

*Growth habit.*—Strong, thick stem with excellent branch angle that holds the large bracts up for a good display of color. Bottom stems break first and elongate faster than upper stems resulting in the upright growth habit, with bract display on upper ⅔ of plant. Growth is vigorous and the plant can easily be grown with use of proper scheduling system without chemical growth regulation.

*Foliage description.*—Leaves are alternate and borne on 5.5 to 6.5 cm long petioles having a reddish purple cast; the last three to four (3–4) leaves before true bract leaves also turn to the same red color as the bracts. Size: Mature leaves are on average 13 to 15 cm long and 9 to 11 cm wide at broadest point near basal area of leaf. Leaves can vary greatly depending on location on plant. Shape: More lanceolate than ovate, with acuminate apex and more truncate than rounded base. Texture: Upper surface glabrous; lower surface glabrous and rugose because of protruding veins. Margin: Entire with slight lobing. Color: Young foliage, top side 144A, underside 146B; mature foliage, top side 147A, underside 147B.

Flowering description (Cyathia):

*Flowering habits.*—Early flowering cultivar, apparently having a longer critical daylength for flower initiation. Under controlled daylength development time is approximately 8½ weeks but temperatures above 70° F. will cause more rapid development without heat delay. Last 3 to 4 true leaves turn red before bract leaves start to develop. Small cyathia area of bract is 2 to 2.5 cm in diameter.

*Natural flowering season.*—November 12 to 17 under Ohio conditons. Flowering time under 11 hours of daylength at 20° C. is 8½ weeks; Red Delight does not heat delay at night temperatures above 23° C.

*Cyathia description.*—In a tight cluster at center of bract and few in number; are stress tolerant, remaining in the involure for a considerable time under low fertility, low light and high temperature conditions even after pollen has shed; severe drying may cause cyathia to drop.

*Cyathia borne.*—Stay tightly clustered without growing apart (splitting), usually 2 to 2.5 cm in diameter. Flowering can be initiated any time of the year by controlling the daylength to approximately eleven (11) hours total; will continue to initiate until daylength is greater than approximately 13 hours.

*Quantity of cyathia.*—Highly dependent on cultural practices and can vary from minimum of 3 to 4 to more than 10.

*Bracts.*—Shape: First true bracts are more ovate, with later formed bracts more lanceolate. First bracts are 11 to 12 cm long and 6 to 8 cm wide with 1 to 2 cm petioles; later bracts are 7 to 8 cm long and 3 to 4 cm wide with 1 cm petioles. Color at maturity: 45A to 45B. Young bract: Similar, except greenish when very immature. Underside: 45C to 45D with midrib and major veins greenish. Number of bracts: 10 to 15 is normal, but could be fewer or more depending on growing conditions. Bract diameter varies with growing conditions, whether plant is pinched, and whether growth regulators are used.

Reproductive organs:

*Stamens.*—Numerous. Anther shape: Oblong. Anther color: Reddish. Filament color: Reddish. Pollen color: Yellow.

*Pistils.*—Stigma shape: Forked. Stigma color: Reddish. Style color: Reddish. Ovaries: Three (3) in number; size 5 mm; color green when stigma is receptive.

Nector cups.—One (1) on most cyathia with two (2) occurring rarely; nectar readily available on mature cyathia.

Disease resistance: Bracts are resistant to botrytis damage; no powdery mildew observed on leaves or bracts; small cyathia area helps prevent botrytis after nectar cups start exuding honey-like substance.

Other Important Characteristics

A. Red Delight has thick strong stems with good branch angles to hold large bracts and provide excellent upright growth habit. This makes sleeving for shipping faster and reduces branch breakage.

B. Can be grown without black cloth for mid-November sales, and can be easily scheduled for later sales by controlling lighting in early stages of development to delay flower bud initiation.

C. Pigments contained in red bract leaves display well under fluorescent lights thus making this cultivar good for mass market sales.

D. With proper scheduling this cultivar can be grown without growth regulators, thereby eliminating both a crop expense and a potential environmental hazard.

It is claimed:

1. A new and distinct poinsettia plant named Red Delight, as illustrated and described.

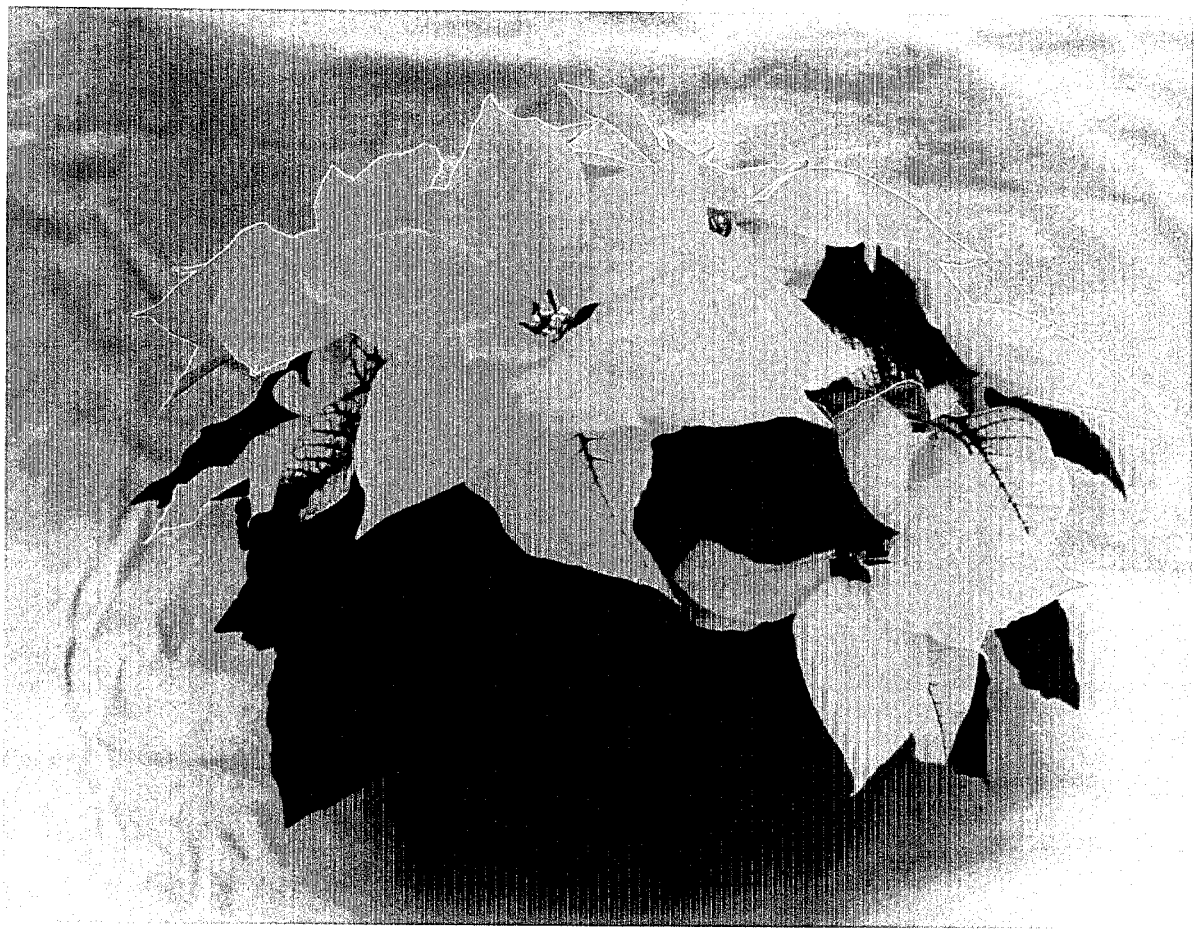

* * * * *